US012742054B2

(12) United States Patent
Dubois

(10) Patent No.: US 12,742,054 B2
(45) Date of Patent: Sep. 22, 2026

(54) RECYCLING OF POLYACETAL FOR THE PRODUCTION OF POLYOXYMETHYLENE DIALKYL ETHERS

(71) Applicant: CHEMCOM INVESTMENTS B.V., Farmsum (NL)

(72) Inventor: Jean-Luc Dubois, Colombes (FR)

(73) Assignee: CHEMCOM INVESTMENTS B.V., Farmsum (NL)

( * ) Notice: Subject to any disclaimer, the term of this patent is extended or adjusted under 35 U.S.C. 154(b) by 702 days.

(21) Appl. No.: 17/916,820

(22) PCT Filed: Apr. 6, 2021

(86) PCT No.: PCT/EP2021/058921

§ 371 (c)(1),
(2) Date: Oct. 4, 2022

(87) PCT Pub. No.: WO2021/204789

PCT Pub. Date: Oct. 14, 2021

(65) Prior Publication Data

US 2023/0151180 A1 May 18, 2023

(30) Foreign Application Priority Data

Apr. 7, 2020 (FR) ................................ FR20.03468

(51) Int. Cl.

| | |
|---|---|
| ***C08G 2/08*** | (2006.01) |
| ***C07C 29/10*** | (2006.01) |
| ***C07C 45/27*** | (2006.01) |
| ***C07C 51/16*** | (2006.01) |
| ***C08G 2/36*** | (2006.01) |
| ***C08J 11/04*** | (2006.01) |
| ***C08J 11/10*** | (2006.01) |
| ***C08J 11/22*** | (2006.01) |

(52) U.S. Cl.

CPC ............... *C08J 11/22* (2013.01); *C07C 29/10* (2013.01); *C07C 45/27* (2013.01); *C07C 51/16* (2013.01); *C08G 2/08* (2013.01); *C08G 2/36* (2013.01); *C08J 11/10* (2013.01); *C08G 2650/12* (2013.01); *C08J 11/04* (2013.01); *C08J 2359/02* (2013.01)

(58) Field of Classification Search

CPC ........ C08G 2/08; C08G 2/36; C08G 2650/12; C08J 11/04; C08J 11/06; C08J 11/10

See application file for complete search history.

(56) References Cited

U.S. PATENT DOCUMENTS

| | | | | |
|---|---|---|---|---|
| 4,118,588 | A * | 10/1978 | Fouquet | C07C 51/353 562/599 |
| H1339 | H * | 7/1994 | Blair | C08G 2/00 528/230 |
| 5,746,785 | A | 5/1998 | Moulton et al. | |
| 6,534,685 | B1 * | 3/2003 | Patrini | C10L 1/1852 568/613 |
| 9,057,034 | B2 * | 6/2015 | Hong | C07C 41/56 |
| 9,067,188 | B2 * | 6/2015 | Chen | B01J 19/2465 |
| 9,365,537 | B2 * | 6/2016 | Haubs | C08J 11/16 |
| 9,469,624 | B2 | 10/2016 | Haubs et al. | |
| 9,546,148 | B2 | 1/2017 | Haubs et al. | |
| 9,574,061 | B2 | 2/2017 | Haubs et al. | |
| 2007/0260094 | A1 * | 11/2007 | Schelling | C08G 2/12 568/600 |
| 2011/0288343 | A1 | 11/2011 | Chen et al. | |
| 2014/0316147 | A1 | 10/2014 | Haubs et al. | |
| 2014/0323686 | A1 | 10/2014 | Kurz et al. | |
| 2014/0329988 | A1 | 11/2014 | Haubs et al. | |
| 2014/0343300 | A1 | 11/2014 | Haubs et al. | |
| 2014/0343301 | A1 | 11/2014 | Haubs et al. | |
| 2014/0343302 | A1 | 11/2014 | Haubs et al. | |
| 2014/0350216 | A1 | 11/2014 | Haubs et al. | |
| 2016/0280882 | A1 | 9/2016 | Haubs et al. | |
| 2021/0114963 | A1 | 4/2021 | Shi et al. | |

FOREIGN PATENT DOCUMENTS

| | | | | | |
|---|---|---|---|---|---|
| CN | 101193948 | A | | 6/2008 | |
| CN | 101668754 | A | * | 3/2010 | C07D 323/06 |
| CN | 102941113 | A | | 2/2013 | |
| CN | 103626640 | A | | 3/2014 | |
| CN | 103319319 | B | * | 11/2015 | C07C 43/303 |
| CN | 107032955 | A | | 8/2017 | |
| CN | 108218678 | A | * | 6/2018 | C07C 41/58 |
| CN | 108291996 | A | | 7/2018 | |
| DE | 10-2004-053839 | A1 | | 5/2006 | |
| DE | 102005002413 | A1 | * | 7/2006 | C08G 2/10 |
| EP | 484786 | A | * | 5/1992 | C07D 323/06 |

(Continued)

OTHER PUBLICATIONS

PL-219274-B1 (Jan. 20, 2014); machine translation in English; abstract not available; equivalent PL-399968-A1 abstract in English is provided. (Year: 2014).*

(Continued)

*Primary Examiner* — Rip A Lee

(74) *Attorney, Agent, or Firm* — Smith, Gambrell & Russell, LLP

(57) ABSTRACT

The present invention relates to a process for recycling polyacetal containing from 8 to 100,000 carbon atoms for the production of a produced polyoxymethylene dialkyl ether of formula R—(OCH2)n-OR', in which R and R' independently represent a methyl group or an ethyl group and n is an integer greater than or equal to 1, the process comprising a step of reacting an acid catalyst with a mixture comprising a polyacetal containing from 8 to 100 000 carbon atoms, a reactive polyoxymethylene dialkyl ether of formula R—(OCH2)k-OR' in which k is an integer greater than or equal to 1, and optionally a solvent.

17 Claims, No Drawings

(56) References Cited

FOREIGN PATENT DOCUMENTS

| | | | | | |
|---|---|---|---|---|---|
| EP | 1 070 755 | A2 | | 1/2001 | |
| EP | 3546441 | A1 | | 10/2019 | |
| FR | 2907779 | A1 | | 5/2008 | |
| GB | 1377083 | A | * | 12/1974 | ............... C08G 2/36 |
| JP | 4273869 | A | * | 9/1992 | ........... C07D 323/06 |
| JP | 2010-523483 | A | | 7/2010 | |
| KR | 10-2014-0107309 | A | | 9/2014 | |
| PL | 173617 | B1 | * | 4/1998 | ........... C08C 47/045 |
| PL | 219274 | B1 | * | 1/2014 | .............. C08J 11/16 |
| WO | WO-9324439 | A1 | * | 12/1993 | ........... C07D 323/06 |
| WO | WO2013076291 | A1 | | 5/2013 | |

OTHER PUBLICATIONS

PL 219274 (Zaklady Azotowe W Tarnowie Moscicach Spolka Akcyjna (PL) Apr. 30, 2015.
Office Communication mailed May 15, 2025 for European Patent Application 21715923.5 (6 pages in French; 6 pages English translation).
Notice of Reasons for Refusal dated Feb. 3, 2026 for Japanese Patent Application No. 2022-561168 (3 pages in Japanese; 3 pages English translation).
Notice of Reasons for Rejection dated Apr. 15, 2025 for Japanese Patent Application No. 2022-561168 (4 pages in Japanese; 5 pages English translation).
Notice to File a Response mailed Nov. 21, 2025 for Korean Patent Application No. 10-2022-7038649 (8 pages in Korean; 9 pages English translation).
First Office Action and Search Report dated Dec. 7, 2023 for Chinese Patent Application No. 202180035313.9 (6 pages in Chinese; 6 pages English translation).
Second Office Action dated Aug. 29, 2024 for Chinese Patent Application No. 202180035313.9 (5 pages in Chinese; 7 pages English translation).
International Search Report mailed Nov. 16, 2021 for International Patent Application No. PCT/EP2021/058921 (6 pages in French; 4 pages English translation).
Written Opinion of the International Searching Authority mailed Nov. 16, 2021 for International Patent Application No. PCT/EP2021/058921 (10 pages in French; 9 pages English translation).

* cited by examiner

RECYCLING OF POLYACETAL FOR THE PRODUCTION OF POLYOXYMETHYLENE DIALKYL ETHERS

CROSS-REFERENCE TO RELATED APPLICATIONS

This application is a national stage application under 35 U.S.C. § 371 of PCT/EP2021/058921, filed Apr. 6, 2021 which claims benefit to application FR 2003468, filed Apr. 7, 2020.

FIELD OF THE INVENTION

The present invention relates to a process for recycling polyacetal for the production of polyoxymethylene dialkyl ethers and to the use of these polyoxymethylene dialkyl ethers for the preparation of (meth)acrylic acid or ester, (meth)acrolein or neopentyl glycol.

TECHNICAL BACKGROUND

The industrial production of polymer materials is constantly increasing. For example, over the last decade, the market demand for polyoxymethylene (POM) polymers, also known as polyacetal or polyformaldehyde, has doubled, leading to an increase in production capacity to 1.7 million tonnes per year in 2015. POMs are used in a wide variety of commercial plastic products such as disposable lighter bodies, sports equipment, toys, pens and also in complex engineering products, particularly in the automotive and electromechanical industries.

After the useful life of these products has expired, the product is discarded and becomes waste. In order to combat plastic pollution, there is thus a need for methods for recycling this type of polymer.

At the present time, POMs can be reused in injection molding processes, but the implementation of these processes is limited by degradation of the materials and the release of formaldehyde, which is harmful to the environment and to health. In addition, the chemical recycling of POMs has not been extensively studied and few approaches focused on POM processing have been implemented.

By way of example, US patent application No. 2014/0343302 describes the processing of POM into cyclic acetal exclusively, in particular into trioxane, in the presence of an aprotic solvent and a catalyst. The cyclic acetal may then be used to produce new POMs. However, the process described in said patent application is intended for POMs which have a relatively small number of repeating units and is thus not suitable for POMs with more varied lengths, which limits its application.

There is thus currently a need for a POM recycling process which is applicable to all types of POMs, notably to those of large size, and which leads to products other than cyclic acetals.

SUMMARY OF THE INVENTION

The present invention arises from the unexpected discovery by the inventor that polyacetal derived from plastic waste can be used in the synthesis of polyoxymethylene dialkyl ethers, with little release of formaldehyde.

The present invention thus relates to a process for recycling polyacetal containing from 8 to 100 000 carbon atoms for the production of a produced polyoxymethylene dialkyl ether of formula R—$(OCH_2)_n$—OR', in which R and R' independently represent a methyl group or an ethyl group and n is an integer greater than or equal to 1, the process comprising a step of reacting an acid catalyst with a mixture comprising a polyacetal containing from 8 to 100 000 carbon atoms, a reactive polyoxymethylene dialkyl ether of formula R—$(OCH_2)_k$—OR' in which R and R' are as defined above and k is an integer greater than or equal to 1, and optionally a solvent.

The present invention also relates to the use of a reactive polyoxymethylene dialkyl ether of formula R—$(OCH_2)_k$—OR' for recycling polyacetal containing from 8 to 100 000 carbon atoms to obtain a produced polyoxymethylene dialkyl ether of formula R—$(OCH_2)_n$—OR'.

The present invention also relates to the use of a produced polyoxymethylene dialkyl ether obtained via the recycling process according to the invention for synthesizing (meth)acrylic acid or ester, (meth)acrolein or neopentyl glycol.

The present invention also relates to a process for synthesizing (meth)acrylic acid or ester or (meth)acrolein or neopentyl glycol, comprising a step of reacting a produced polyoxymethylene dialkyl ether obtained via the recycling process according to the invention.

DETAILED DESCRIPTION OF THE INVENTION

Polyacetal

The process according to the invention is a process for recycling polyacetal.

The term "polyacetal" means a homopolymer or copolymer based on formaldehyde. The polyacetal may be a mixture of homopolymers and/or copolymers based on formaldehyde.

For the purposes of the present invention, the term "homopolymer" means a formaldehyde polymer also known as polyoxymethylene (POM) or polyformaldehyde. A homopolymer is generally in the form of a mixture of homopolymers of different chain lengths.

For the purposes of the present invention, the term "copolymer" means a polymer of formaldehyde and of one or more monomers other than formaldehyde. A copolymer is generally in the form of a mixture of copolymers of different chain lengths.

According to one embodiment, the polyacetal is a mixture of homopolymer and copolymer. Preferably, the mixture of homopolymer and copolymer comprises less than 20%, preferably less than 15%, less than 10%, less than 9%, less than 8%, less than 7% or less than 6%, more preferably less than 5%, less than 4%, less than 3%, less than 2% or less than 1%, by weight of copolymer relative to the weight of the mixture of homopolymer and copolymer.

According to another embodiment, the polyacetal is a homopolymer.

The polyacetal may have a number of carbon atoms ranging from 8 to 100 000, from 8 to 50 000, from 8 to 10 000 or from 8 to 100. Alternatively, the polyacetal may have a number of carbon atoms ranging from 100 to 100 000, from 500 to 100 000, from 1000 to 100 000, from 1000 to 50 000, from 3000 to 50 000 or from 3000 to 10 000.

The polyacetal can be derived from various waste materials; it is then referred to as post-production or post-industrial polyacetal or post-consumer polyacetal. By way of example, the polyacetal may be derived from waste products from the automotive, aeronautical, telecommunication, sports, leisure, electronic, electromechanical, etc. industries.

The polyacetal may also comprise additives such as glass fibers, carbon fibers, carbon nanotubes, carbon black, pigments, etc. The polyacetal may also be contaminated with other polymers or contaminants, but, in this case, the waste to be recycled is chosen such that these other polymers/contaminants are inert in the recycling process, i.e. they do not dissolve and/or react during the reaction.

Preferably, the polyacetal is ground so as to obtain polyacetal pieces of 0.05 to 2 cm. Preferably, the polyacetal pieces obtained after grinding do not exceed 1.5 cm, 1 cm, 0.8 cm, 0.5 cm, 0.3 cm, 0.2 cm, 0.1 cm or 0.05 cm. Preferably, the ground polyacetal pieces are dried via any method that is well known to those skilled in the art so as to remove any traces of residual water. By way of example, the polyacetal pieces may be dried under vacuum or under a stream of nitrogen at a temperature preferably ranging from 20° C. to 100° C., more preferably from 60° C. to 100° C., for a time preferably ranging from 2 to 30 hours, more preferably from 5 to 60 hours. Alternatively, the polyacetal may be dried under microwave flow, for a period of less than 30 minutes, preferably less than 10 minutes.

Polyoxymethylene Dialkyl Ethers

Polyoxymethylene dialkyl ethers are designated by the acronym POM for PolyOxyMethylene followed by one or more characters for identifying the alkyl radicals R and R' (POMX with X=M for methyl, E for ethyl or M/E for a mixture of methyl and ethyl), and also an integer corresponding to the number of —($CH_2O$)— units (n in the case of produced polyoxymethylene dialkyl ether ($POMX_n$) and k in the case of reactive polyoxymethylene dialkyl ether ($POMX_k$)).

In the present invention, a distinction is made between the terms "produced polyoxymethylene dialkyl ether(s)" and "reactive polyoxymethylene dialkyl ether(s)".

A produced polyoxymethylene dialkyl ether (or $POMX_n$ with X=M when R and R' are methyl, X=E when R and R' are ethyl or X=M/E when R and R' are a mixture of methyl and ethyl) is a polyoxymethylene dialkyl ether obtained via the polyacetal recycling process according to the invention.

A reactive polyoxymethylene dialkyl ether (or $POMX_k$ with X=M when R and R' are methyl, X=E when R and R' are ethyl or X=M/E when R and R' are a mixture of methyl and ethyl) is a polyoxymethylene dialkyl ether used as reagent in the recycling process according to the invention to obtain a produced polyoxymethylene dialkyl ether.

Produced Polyoxymethylene Dialkyl Ether

The process according to the invention provides a produced polyoxymethylene dialkyl ether from polyacetal, reactive polyoxymethylene dialkyl ether and an acid catalyst. The produced polyoxymethylene dialkyl ether may notably comprise polyoxymethylene dialkyl ether derived from the depolymerization of polyacetal and optionally reactive polyoxymethylene dialkyl ether.

The produced polyoxymethylene dialkyl ether corresponds to the formula R—($OCH_2$)$_n$—OR', in which R and R' independently represent a methyl group or an ethyl group and n is an integer greater than or equal to 1.

The produced polyoxymethylene dialkyl ether may be recovered from the process according to the invention, notably by a separation step, for example a distillation step. The recovery step makes it possible to isolate the produced polyoxymethylene dialkyl ether from the remaining reaction mixture. The recovery step is detailed below.

The produced polyoxymethylene dialkyl ether may be a $POMX_n$ with a specific n value or a mixture of $POMX_n$ with different n values. Preferably, the produced polyoxymethylene dialkyl ether is a mixture of $POMX_n$.

By way of example, the following names are used for the produced polyoxymethylene dialkyl ether:

- $POMM_n$ (polyoxymethylene dimethyl ether) when the alkyl is a methyl group, and for example $POMM_1$ when n=1, also known as methylal or dimethoxymethane (DMM);
- $POME_n$ (polyoxymethylene diethyl ether) when the alkyl is an ethyl group, and for example $POME_1$ when n=1, also known as ethylal; and
- $POMM/E_n$ (polyoxymethylene methyl ethyl ether) when the alkyl is a mixture of methyl and ethyl groups.

The process according to the invention makes it possible to obtain $POMM_n$s, $POME_n$s and $POMM/E_n$s of all ranks simultaneously, i.e. from n=1 to infinity. However, polyoxymethylene dialkyl ethers of rank n greater than 8 are difficult to detect and quantify via conventional analytical methods.

Preferably, the produced polyoxymethylene dialkyl ether has a number n ranging from 1 to 100, preferably from 1 to 50, from 1 to 25 or from 1 to 15, more preferably from 1 to 10, even more preferably from 1 to 8.

Preferably, the produced polyoxymethylene dialkyl ether comprises less than 10% by weight of polyoxymethylene dialkyl ether having a number n greater than 8, more preferably less than 9%, less than 8%, less than 7%, less than 6%, less than 5%, less than 4%, less than 3%, less than 2%, by weight of polyoxymethylene dialkyl ether having a number n greater than 8, relative to the total weight of produced polyoxymethylene dialkyl ether.

The produced polyoxymethylene dialkyl ether may comprise methylal and/or ethylal originating at least partly from the reactive polyoxymethylene dialkyl ether introduced at the start of the process with the polyacetal. The methylal and/or ethylal may advantageously be separated from the rest of the produced polyoxymethylene dialkyl ether by an evaporation step, for example by distillation, and may optionally be recycled to the start of the process as reactive polyoxymethylene dialkyl ether by a recycling step. The evaporation and recycling steps are described below.

Preferably, the produced polyoxymethylene dialkyl ether is a $POMM_{2-8}$ or $POME_{2-8}$ or $POMM/E_{2-8}$ mixture, i.e. a mixture containing $POMM_n$s or $POME_n$s or $POMM/E_n$s in which n ranges from 2 to 8 (notably after a step of separation from $POMX_1$).

Preferably, the produced polyoxymethylene dialkyl ether is chosen from the group consisting of $CH_3$—($OCH_2$)—$OCH_3$, $CH_3$—$(OCH_2)_2$—$OCH_3$, $CH_3$—$(OCH_2)_3$—$OCH_3$, $CH_3$—$(OCH_2)_4$—$OCH_3$, $CH_3$—$(OCH_2)_5$—$OCH_3$, $CH_3$—$(OCH_2)_6$—$OCH_3$, $CH_3$—$(OCH_2)_7$—$OCH_3$, $CH_3$—$(OCH_2)_8$—$OCH_3$, $C_2H_5$—($OCH_2$)—$OC_2H_5$, $C_2H_5$—$(OCH_2)_2$—$OC_2H_5$, $C_2H_5$—$(OCH_2)_3$—$OC_2H_5$, $C_2H_5$—$(OCH_2)_4$—$OC_2H_5$, $C_2H_5$—$(OCH_2)_5$—$OC_2H_5$, $C_2H_5$—$(OCH_2)_6$—$OC_2H_5$, $C_2H_5$—$(OCH_2)_7$—$OC_2H_5$, $C_2H_5$—$(OCH_2)_8$—$OC_2H_5$ and mixtures thereof.

Preferably, the produced polyoxymethylene dialkyl ether is a $POMM_{2-8}$ which is a mixture of compounds of formula $CH_3$—$(OCH_2)_n$—$OCH_3$ with n=2 to 8. Preferably, the composition of the $POMM_{2-8}$ is as follows:

TABLE 1

| n | 2 | 3 | 4 | 5 | 6 | 7 | 8 |
|---|---|---|---|---|---|---|---|
| wt % | 25-50 | 20-40 | 10-25 | 5-15 | 2-10 | 1-7 | 0-2 |

More particularly, a preferred composition of a $POMM_{2-8}$ compound is as follows:

TABLE 2

| n | 2 | 3 | 4 | 5 | 6 | 7 | 8 |
|---|---|---|---|---|---|---|---|
| wt % | 44 | 32 | 14 | 6 | 2.5 | 1 | <1 |

According to one embodiment, the produced polyoxymethylene dialkyl ether is a $POMM_{2-4}$ which is a mixture of compounds of formula $CH_3$—$(OCH_2)_n$—$OCH_3$ with n=2 to 4. Preferably, the composition of the $POMM_{2-4}$ is as follows:

TABLE 3

| | n | | |
|---|---|---|---|
| | 2 | 3 | 4 |
| wt % | 50-70 | 15-35 | 5-15 |

According to one embodiment, the produced polyoxymethylene dialkyl ether is a $POMM_{3-4}$ which is a mixture of compounds of formula $CH_3$—$(OCH_2)_n$—$OCH_3$ with n=3 to 4. Preferably, the composition of the $POMM_{3-4}$ is as follows:

TABLE 4

| | n | |
|---|---|---|
| | 3 | 4 |
| wt % | 50-70 | 30-50 |

According to one embodiment, the produced polyoxymethylene dialkyl ether is a $POMM_{3-5}$ which is a mixture of compounds of formula $CH_3$—$(OCH_2)_n$—$OCH_3$ with n=3 to 5. Preferably, the composition of the $POMM_{3-5}$ is as follows:

TABLE 5

| | n | | |
|---|---|---|---|
| | 3 | 4 | 5 |
| wt % | 40-60 | 20-40 | 10-30 |

According to one embodiment, the produced polyoxymethylene dialkyl ether is a $POME_{2-4}$ which is a mixture of compounds of formula $C_2H_5$—$(OCH_2)_n$—$OC_2H_5$ with n=2 to 4.

Reactive Polyoxymethylene Dialkyl Ether

The reactive polyoxymethylene dialkyl ether is placed in contact with the polyacetal and an acid catalyst to obtain the produced polyoxymethylene dialkyl ether.

The reactive polyoxymethylene dialkyl ether according to the invention corresponds to the formula R—$(OCH_2)_k$—OR' in which R and R' independently represent a methyl group or an ethyl group and k is an integer greater than or equal to 1. Preferably, k is an integer ranging from 1 to 100, preferably from 1 to 50, from 1 to 25 or from 1 to 15, more preferably from 1 to 10, even more preferably from 1 to 8.

The reactive polyoxymethylene dialkyl ether may be a $POMX_k$ with a specific k value or a mixture of $POMX_k$ with different k values.

Preferably, the reactive polyoxymethylene dialkyl ether comprises methylal and/or ethylal.

According to a particular embodiment of the invention, the reactive polyoxymethylene dialkyl ether comprises non-recycled methylal and/or ethylal (also known as fresh methylal and/or ethylal). For the purposes of the present invention, a non-recycled compound (or a fresh compound) is a compound which does not originate from a recycling step of the process.

The fresh methylal and/or ethylal may notably be used to initiate the process according to the invention. Once the process is running, the methylal and/or ethylal may be separated from the produced polyoxymethylene dialkyl ether by an evaporation step, for example by distillation, and may optionally be recycled to the start of the process as reactive polyoxymethylene dialkyl ether by a recycling step. The evaporation and recycling steps are described below.

Thus, the reactive polyoxymethylene dialkyl ether may comprise recycled methylal and/or ethylal. For the purposes of the present invention, a recycled compound is a compound which originates from a recycling step of the process.

Preferably, the reactive polyoxymethylene dialkyl ether comprises recycled methylal and/or ethylal and also fresh methylal and/or ethylal.

The reactive polyoxymethylene dialkyl ether may comprise one or more $POMX_k$ with a k number of greater than or equal to 2. By way of example, the reactive polyoxymethylene dialkyl ether may comprise compounds chosen from $POMM_2$, $POMM_3$, $POMM_4$, $POMM_5$, $POMM_6$, $POMM_7$, $POMM_8$, POMMs of higher rank, $POME_2$, $POME_3$, $POME_4$, $POME_5$, $POME_6$, $POME_7$, $POME_8$, POMEs of higher rank and mixtures thereof. These compounds may be fresh or recycled.

Preferably, the reactive polyoxymethylene dialkyl ether comprises methylal and/or ethylal and also one or more $POMX_k$s with a k greater than or equal to 2.

In one embodiment of the present invention, the reactive polyoxymethylene dialkyl ether comprises only fresh methylal and/or ethylal.

In another embodiment of the invention, the reactive polyoxymethylene dialkyl ether comprises fresh methylal and/or ethylal and also recycled methylal and/or ethylal.

In another embodiment of the invention, the reactive polyoxymethylene dialkyl ether comprises fresh methylal and/or ethylal, optionally recycled methylal and/or ethylal, and also a mixture of fresh or recycled $POMX_k$ with a k number of greater than or equal to 2.

Preferably, the ratio of the mass of the reactive polyoxymethylene dialkyl ether to the mass of the polyacetal is at least 2:1, preferably at least 2.5:1, at least 3:1, at least 5:1, at least 6:1, at least 7:1, at least 8:1 or at least 9:1.

Preferably, the reactive polyoxymethylene dialkyl ether comprises less than 5%, preferably less than 4%, less than 3%, less than 2% or less than 1%, by weight of $POMX_k$ with a k greater than 8 relative to the total weight of $POMX_k$ with a k greater than or equal to 2.

Polyacetal Recycling Process

The process according to the invention comprises a step of reaction between an acid catalyst and a mixture comprising a polyacetal as defined above, a reactive polyoxymethylene dialkyl ether as defined above and optionally a solvent.

The presence of solvent depends on the nature of the reactive polyoxymethylene dialkyl ether used. Indeed, the reaction mixture must be at least partly liquid in order for the reaction to take place. For the purposes of the present invention, a liquid mixture means a mixture that is capable of flowing under its own weight at room temperature (20° C.). The reaction mixture may be a dispersion, i.e. a system containing solid pieces of polyacetal dispersed in a liquid phase. Indeed, the polyacetal is generally in solid form and can be at least partially dissolved by the reactive polyoxymethylene dialkyl ether and optionally a solvent. The solvent advantageously facilitates the dissolution of the polyacetal.

When only methylal and/or ethylal is used as reactive polyoxymethylene dialkyl ether, the presence of a solvent is not necessary.

Preferably, the solvent is chosen to have a boiling point higher than the boiling point of the produced polyoxymethylene dialkyl ether that it is desired to obtain. Preferably, the solvent is chosen to have a boiling point higher than the boiling point of the produced polyoxymethylene dialkyl ether having a number n=1 to 8. Preferably, the solvent has a boiling point higher than the boiling point of the produced polyoxymethylene dialkyl ether having the highest n value, which it is desired to recover. The other high-boiling POMs can then be recycled with the solvent to the start of the process by a recycling step. Preferably, the solvent has a boiling point of greater than 120° C. under partial vacuum (i.e. at about 10 mmHg), or a boiling point of greater than 250° C. corrected for atmospheric pressure.

The solvent may notably be chosen from sulfolane, methylsulfolane, ethylsulfolane, diethylsulfolane, propylsulfolane, dipropylsulfolane, butylsulfolane, dibutylsulfolane, pentylsulfolane, dipentylsulfolane, hexylsulfolane, octylsulfolane, DMSO and mixtures thereof. Preferably, the solvent is sulfolane.

By way of example, sulfolane has a boiling point of 285° C., methylsulfolane has a boiling point of 278° C. and DMSO has a boiling point of 189° C., under standard temperature and pressure conditions (25° C. and atmospheric pressure).

Preferably, the solvent is added in an amount ranging from 20% to 80%, more preferably from 30% to 70%, even more preferably from 40% to 60% by mass of solvent relative to the total mass of the mixture. Preferably, the amount of solvent in the mixture is about 50% by mass relative to the total mass of the solvent+reactive polyoxymethylene dialkyl ether mixture.

Preferably, the mixture is dissolved at a temperature below 120° C., preferably from 20° C. to 120° C., more preferably from 40° C. to 110° C., preferably at a pressure ranging from atmospheric pressure to 10 bar.

The acid catalyst may be a homogeneous or heterogeneous catalyst. Preferably, the catalyst is a heterogeneous catalyst. The use of a heterogeneous catalyst advantageously facilitates its removal by filtration on conclusion of the reaction step.

As examples of catalysts that are suitable for use in the process according to the invention, mention may be made of acidic resins, for example Amberlyst® and Lewatit® type resins, Lewis acids and Brønsted acids. For the purposes of the present invention, an acidic resin is a macroporous polymeric cation-exchange resin (for example a styrene-divinylbenzene copolymer) that is capable of supplying $H^+$ ions.

Preferably, the catalyst is chosen from the group consisting of acidic resins; organic or mineral acids such as trifluoromethanesulfonic acid, perchloric acid, methanesulfonic acid, para-toluenesulfonic acid, and sulfuric acid; Lewis acids such as $BF_3$, $AsF_5$; acidic mixed oxides, such as $WO_3/TiO_2$, phosphate alumina, tungsten alumina, and zeolites; and mixtures thereof.

In one embodiment of the invention, the polyacetal is, in a first stage, at least partially dissolved with the reactive polyoxymethylene dialkyl ether and optionally a solvent, and the mixture is then placed in contact with the acid catalyst.

In another embodiment of the invention, the polyacetal is, in a first stage, placed in contact with the acid catalyst and a solvent, and the reactive polyoxymethylene dialkyl ether is then added.

Preferably, in the case of a homogeneous catalyst, said catalyst is present in an amount ranging from 0.01 to 10 mol per kg of polyacetal, preferably from 0.02 to 5, more preferentially from 0.05 to 2 mol per kg of polyacetal.

Preferably, the reaction performed in the presence of the acid catalyst is performed at a temperature below 120° C., preferably from 20° C. to less than 120° C., more preferably from 40° C. to 115° C. or from 60 to 110° C. and even more preferably from 80° C. to 110° C., at a pressure ranging from 1 to 10 bar and preferably from 5 to 10 bar to avoid boiling of the mixture.

The reaction may be performed in batch mode or in continuous mode. In the batch configuration, the catalyst is preferably stirred with the mixture, but it may also be placed in a wire basket, which is itself rotated in the reactor. In the continuous mode, the catalyst is preferably placed in a fixed or fluidized bed. The mixture containing the polyacetal, the reactive polyoxymethylene dialkyl ether and optionally the solvent flows through the catalyst bed from top to bottom or from bottom to top. Preferably, the liquid flows through the catalyst bed from bottom to top, and the catalyst grains retain mobility in the catalyst bed, without, however, being entrained.

The process according to the invention may comprise a filtration step. In one embodiment of the invention, a step of filtration of the mixture is performed before the reaction step with the acid catalyst so as to retain any contaminants, namely the additives present in the polyacetal and/or undissolved polyacetal pieces, mineral fillers such as glass or carbon fibers, or other undissolved polymers. In another embodiment of the invention, a filtration step is performed prior to the formation of the mixture comprising the polyacetal with at least one reactive polyoxymethylene dialkyl ether and optionally a solvent. In this case, the polyacetal is at least partially dissolved in a suitable solvent and a filtration step is performed so as to remove any contaminants, namely the additives present in the polyacetal, and/or undissolved polyacetal pieces, mineral fillers such as glass or carbon fibers, or other undissolved polymers. A person skilled in the art will know which solvent is able to dissolve the polyacetal. As examples of suitable solvents, mention may be made of the solvents defined above. In another embodiment of the invention, a filtration step is performed after the mixture has been placed in contact with a catalyst and optionally neutralized, so as to remove the solid particles, notably any contaminants, namely the additives present in the polyacetal, and/or undissolved polyacetal pieces, mineral fillers such as glass or carbon fibers, other undissolved polymers and/or acidic or anionic resin particles.

The process according to the invention may comprise a catalyst separation step. The optional catalyst separation step is performed after the reaction step. The optional catalyst separation step may be performed by filtration or centrifugation when the acid catalyst is dispersed in the reaction medium. Alternatively, if the acid catalyst is contained in a wire basket, it suffices to remove the wire basket from the reactor. When the reaction is performed in continuous mode with an acid catalyst in a fixed bed, the separation step is not necessary since the catalyst remains trapped in the fixed bed.

The process according to the invention may comprise a neutralization step. The optional neutralization step is performed after the reaction step. The optional neutralization step may be performed with a base so as to remove any traces of residual acid. Any base well known to those skilled in the art may be used for this purpose. By way of example, an aqueous sodium hydroxide solution, a methanolic sodium hydroxide solution, sodium or potassium methoxide, a solution of sodium hydroxide in methylal, anhydrous sodium hydroxide, potassium hydroxide, lime, an aqueous ammonia solution, triethylamine, diisopropylethylamine, melamine, or an anionic resin such as Ambersep 900 OH resin may be used for this purpose. Preferably, the base is anhydrous.

After the reaction step, the reaction mixture contains a distribution of polyoxymethylene dialkyl ethers of all ranks, i.e. $POMX_n$s with n=1 to infinity.

The process according to the invention may comprise an evaporation step. The evaporation step allows all or part of the light compounds to be removed, notably the $POMX_n$s with n=1 and possibly n=2. The light compounds are removed at the top of the evaporation unit. The evaporation step may be performed with an evaporation unit chosen from a rotary evaporator and/or a distillation column. The evaporation may be performed in one step or in several successive steps. The evaporation step is preferably a step of distillation at atmospheric pressure or under reduced pressure at a lower temperature, for example at a temperature below 120° C., preferably below 110° C. at atmospheric pressure, or under a reduced pressure, for example ranging from 0.4 to 0.6 atm. Some or all of the light compounds removed during the evaporation step may be reintroduced into the reaction step as reactive polyoxymethylene dialkyl ether.

The process according to the invention may comprise a step of recovering the produced polyoxymethylene dialkyl ether. The recovery step allows the separation of the produced polyoxymethylene dialkyl ether, notably the $POMX_n$s with a number n greater than or equal to 2, or 3, preferably with n=2 to 8, 2 to 5, 2 to 4, 3 to 5 or 3 to 4, from the rest of the reaction mixture. In particular, the recovery step may allow the separation of the produced polyoxymethylene dialkyl ether from the heavy compounds. The heavy compounds may be $POMX_n$s with n greater than the maximum n value of the produced polyoxymethylene dialkyl ether, notably greater than 4, greater than 5, greater than 6, greater than 7, greater than 8 or greater than 10. The recovery step may notably be performed by distillation. The heavy compounds remain in the distillation tail fraction and the desired produced polyoxymethylene dialkyl ether is collected in the distillation head fraction. The distillation is preferentially performed under partial vacuum. The heating temperature is advantageously maintained below 120° C. Indeed, heating above 120° C. could degrade the produced polyoxymethylene dialkyl ether. The vacuum level and the heating temperature are adjusted so as to distil off the $POMX_n$s of the targeted chain length. The distillation may be performed under partial vacuum, at a pressure preferably ranging from 5 mbar to 60 mbar. The temperature-pressure pair which corresponds to the produced polyoxymethylene dialkyl ether that it is desired to obtain can be readily selected by a person skilled in the art. Some or all of the heavy compounds removed during the distillation step may be reintroduced into the reaction step as reactive polyoxymethylene dialkyl ether.

The process according to the invention may comprise a recycling step. The recycling step may notably make it possible to reintroduce into the reaction step a portion of the compounds of formula R—$(OCH_2)_n$—OR' with n greater than or equal to 1 contained in the reaction mixture. These compounds may be used as reactive polyoxymethylene dialkyl ether. In particular, the recycling step makes it possible to reintroduce all or some of the light compounds removed in the evaporation step and/or all or some of the heavy compounds removed in the recovery step into the reaction step as reactive polyoxymethylene dialkyl ether. Preferably, the methylal ($POMM_1$) and/or ethylal ($POME_1$) recovered during the evaporation step is reintroduced into the reaction step as reactive polyoxymethylene dialkyl ether. After the desired produced polyoxymethylene dialkyl ether has been recovered, some or all of the heavy compounds, preferably $POMX_n$ with a number n less than 8, may also be reintroduced into the reaction step as reactive polyoxymethylene dialkyl ether.

When a solvent is used in the process, it generally remains at the bottom of the column and can be reused as solvent in the process according to the invention, possibly with the higher-ranking polyoxymethylene dialkyl ethers, notably having a number n greater than 8, which it contains.

The produced polyoxymethylene dialkyl ether obtained via the recycling process according to the invention may be used as starting material for the synthesis of other organic compounds, notably (meth)acrylic acid or ester, (meth) acrolein or neopentyl glycol.

Thus, the process according to the invention may comprise a step of synthesizing (meth)acrylic acid or ester or (meth)acrolein or neopentyl glycol from the produced polyoxymethylene dialkyl ether.

The synthesis of (meth)acrylic acid or ester or (meth) acrolein or neopentyl glycol may be performed under the conditions described below.

Use of a Produced Polyoxymethylene Dialkyl Ether Obtained Via the Recycling Process The produced polyoxymethylene dialkyl ether obtained via the polyacetal recycling process according to the invention may be used as a substitute or additive for diesel fuel, as a substitute for methanol in fuel cells and also for preserving the human or animal body and/or for embalming dead bodies.

Moreover, the produced polyoxymethylene dialkyl ether obtained via the polyacetal recycling process according to the invention, notably $POMM_{2-8}$, $POME_{2-8}$ or $POMM/E_{2-8}$ optionally as a mixture with methylal and/or ethylal, may be used as reagents or synthetic intermediates, notably for synthesizing (meth)acrylic acid or ester or (meth)acrolein or neopentyl glycol.

The synthesis of (meth)acrylic acid or ester or (meth) acrolein is preferably performed via an aldol condensation reaction. Preferably, the synthesis of (meth)acrylic acid or ester or (meth)acrolein is performed by reacting a produced polyoxymethylene dialkyl ether obtained via the polyacetal recycling process according to the invention with a suitable carboxylic acid or ester or a saturated aldehyde in the presence of a catalyst.

Preferably, the produced polyoxymethylene dialkyl ether is a mixture of $POMX_n$ with a number n=1 to 100, more preferably 1 to 50, 1 to 20 or 1 to 10 and even more preferably 1 to 8. Advantageously, the produced polyoxymethylene dialkyl ether avoids the use of free formaldehyde, which simplifies the separation of the (meth)acrylic acid or ester or (meth)acrolein produced.

The carboxylic acids and esters that may be used for synthesizing (meth)acrylic acid or ester or (meth)acrolein are well known to those skilled in the art. As examples of carboxylic acids, mention may be made of propionic acid and acetic acid. As examples of esters, mention may be made of propanoic acid esters, such as methyl propionate, ethyl propionate, propyl propionate and butyl propionate, or methyl acetate. As examples of aldehydes, mention may be made of acetaldehyde and propanaldehyde.

The catalyst used for synthesizing (meth)acrylic acid or ester or (meth)acrolein may be chosen from any acidic or basic catalyst that is well known to those skilled in the art for this type of reaction. As examples of suitable catalysts, mention may be made of catalysts based on magnesium, calcium, aluminum, zirconium or thorium phosphates and/or silicates, strontium hydroxyapatite, barium hydroxyapatite, a silica doped with an alkali metal or an alkaline-earth metal and/or zirconium, calcium hydroxyapatite and a mixture thereof.

It is also possible to add an alcohol to the process for synthesizing (meth)acrylic acid or ester or (meth)acrolein. This alcohol may serve as solvent for the reaction. Any alcohol that is well known to those skilled in the art for this type of synthesis may be used. As examples of suitable alcohols, mention may be made of methanol, ethanol, propanol, isopropanol, isobutanol, t-butyl alcohol, phenol, n-butanol and chlorocapryl alcohol.

The synthesis of neopentyl glycol is preferably performed via an aldol condensation reaction. Preferably, neopentyl glycol is synthesized by reacting a produced polyoxymethylene dialkyl ether obtained via the polyacetal recycling process according to the invention with isobutyraldehyde.

Preferably, the produced polyoxymethylene dialkyl ether is a mixture of $POMX_n$ with a number n=1 to 100, more preferably 1 to 50, 1 to 20 or 1 to 10 and even more preferably 1 to 8.

Preferably, the neopentyl glycol synthesis is catalyzed with a tertiary alkylamine compound.

It is also possible to add an alcohol to the neopentyl glycol synthesis process. This alcohol may serve as solvent for the reaction. Any alcohol that is well known to those skilled in the art for this type of synthesis may be used. An example of a suitable alcohol that may be mentioned is methanol.

The present invention is illustrated with the aid of the nonlimiting examples that follow.

EXAMPLES

Example 1: Production of $POMM_{2-8}$ 375 kg of post-production polyacetal homopolymer, previously ground into pieces not exceeding 1 cm and dried under vacuum at 80° C. to remove any residual traces of water, are added to 475 kg of fresh dimethoxymethane ($POMM_1$) sold by the company Lambiotte (Belgium), at room temperature in an autoclave. 475 kg of $POMM_1$ obtained from the distillation of a previous recycling step are also added cold (20° C.) to the autoclave. The autoclave is then closed and heated to 100° C. The pressure in the autoclave gradually increases and then stabilizes at less than 6 bar with the temperature. After about 30 minutes, the dissolved mixture is sent to the reactor, passing over a filter which retains any contaminants and/or undissolved polymer.

In the reactor, a bed of Amberlyst® 15Dry acidic resin (DuPont) was placed on top of a grid. The Amberlyst® 15Dry resin (1325 kg) was first washed with methanol and then dimethoxymethane so as to remove any residual traces of water. The previously dissolved mixture is sent to the reactor in ascending stream mode. It is dispersed through the catalytic bed via the bottom distribution plate. The acidic resin beads are free to move when the reactor is used in ascending stream mode, but the linear velocity of the liquid is not sufficient to entrain any catalytic particles. The residence time of the liquid mixture in the reactor, i.e. the ratio of the volume of resin (catalytic bed of resin) to the flow rate of polyacetal solution in the $POMM_1$, is 1 hour. The temperature of the solution which feeds the reactor is kept below 120° C. and notably at 115° C. The reactor is operated under a pressure of 10 bar to prevent any boiling of the reaction solution.

The reaction mixture is then sent to a distillation column. The pressure is reduced to atmospheric pressure and the temperature is lowered to 25° C. A concentrated sodium hydroxide solution is added to neutralize the traces of acidic resin that have been entrained with the reaction mixture. The mixture is then conveyed into the distillation step.

The temperature at the top of the column is 42° C., and 80° C. at the bottom. At the top of the column, the dimethoxymethane is obtained, condensed, and returned to the dissolution autoclave (475 kg) for the next operation. The mixture of $POMM_{2-8+}$ is obtained at the bottom of the column. A mixture containing 331 kg of $POMM_2$, 212 kg of $POMM_3$, 130 kg of $POMM_4$, 76 kg of $POMM_5$, 44 kg of $POMM_6$, 25 kg of $POMM_7$, 14 kg of $POMM_8$ and 16 kg of POMMs of higher rank is obtained, determined by chromatographic analysis.

Example 2: Production of $POMM_{3-4}$ 375 kg of post-production polyacetal homopolymer, previously ground into pieces not exceeding 0.5 cm and dried under vacuum at 80° C., are added to 399 kg of fresh dimethoxymethane ($POMM_1$), at room temperature in an autoclave.

1799 kg of light mixture of $POMM_1$ (1060 kg) and of $POMM_2$ (739 kg) obtained from a previous operation, and 394 kg of a mixture of POMMs from a previous operation containing 171 kg of $POMM_5$, 98 kg of $POMM_6$, 56 kg of $POMM_7$, 31 kg of $POMM_8$ and 37 kg of POMMs of higher rank, are also added.

The autoclave is then closed and heated to 110° C. The pressure in the autoclave gradually increases and then stabilizes with the temperature. After about 45 minutes, the dissolved mixture is sent to the reactor, passing over a filter which retains any contaminants and/or undissolved polymer.

In the reactor of example 1, a bed of Amberlyst® 15Dry acidic resin was placed on top of a grid. During the first operation, the Amberlyst® 15Dry resin was first washed with methanol and then with dimethoxymethane so as to remove any residual traces of water. In the subsequent operations, this washing is no longer necessary if the resin has not been contaminated with water.

The previously dissolved mixture is sent to the reactor in ascending stream mode. It is dispersed through the catalytic bed via the bottom distribution plate. The acidic resin beads are free to move when the reactor is used in ascending stream mode, but the linear velocity of the liquid is not sufficient to entrain any catalytic particles. The residence time of the liquid mixture in the reactor, i.e. the ratio of the volume of resin (catalytic bed of resin) to the flow rate of polyacetal solution in the $POMM_1$, is 1 hour. The temperature of the solution which feeds the reactor is kept below 120° C., notably 110° C. The reactor is operated under a pressure of 10 bar to prevent any boiling of the reaction solution.

The reaction mixture is then sent to a distillation column. The pressure is returned to atmospheric pressure. Triethylamine is injected into the solution to neutralize the acidity caused by the presence of fine catalytic particles (Amberlyst® resin) which are entrained from the reactor.

The temperature at the top of the column is 106° C., and 120° C. at the bottom. At the top of the column, a mixture of dimethoxymethane, $POMM_1$ and $POMM_2$ is obtained, condensed, and returned to the dissolution autoclave (1799 kg of light mixture of $POMM_1$ (1060 kg) and $POMM_2$ (739 kg). The mixture of $POMM_{3+}$ is obtained at the bottom of the column. The column bottom fraction is then sent to another distillation column operated under partial vacuum (60 mbar). The mixture of $POMM_3$ and $POMM_4$ is distilled and condensed; 763 kg of a mixture of $POMM_3$ (474 kg) and $POMM_4$ (289 kg) are then obtained. The mixture of higher POMMs is recovered at the bottom of the column. 171 kg of $POMM_5$, 98 kg of $POMM_6$, 56 kg of $POMM_7$, 31 kg of $POMM_8$, and 37 kg of POMMs of higher rank are obtained and returned to the dissolution autoclave.

Example 3: Production of $POMM_{3-5}$ 375 kg of post-production polyacetal homopolymer, previously ground into pieces not exceeding 0.8 cm, and dried under vacuum at 70° C. for 24 hours, are added to 364 kg of fresh dimethoxymethane, at room temperature in an autoclave.

1407 kg of a light mixture of $POMM_1$ (829 kg) and $POMM_2$ (578 kg) obtained from a previous operation, and 174 kg of a mixture of heavy POMMs from a previous operation containing 77 kg of $POMM_6$, 44 kg of $POMM_7$, 24 kg of $POMM_8$ and 29 kg of POMMs of higher rank are also added.

The autoclave is then closed and heated to 100° C. The pressure in the autoclave gradually increases and then stabilizes with the temperature. After about 60 minutes, the dissolved mixture is sent to the reactor, passing over a filter which retains any contaminants and/or undissolved polymer.

1 kg of anhydrous methanesulfonic acid is injected into the reactor, which is a pressurized stirred reactor on which is mounted a condenser, operated at 100° C. The reaction is continued for 1 hour, the temperature is then reduced to 30° C. and maintained for 30 minutes, the pressure is returned to atmospheric pressure, and an Ambersep® 900 OH anionic resin is injected to neutralize the acid catalyst. The reaction mixture is then filtered to remove the solid particles and is sent to a distillation column.

The temperature at the top of the column is 105° C., and 120° C. at the bottom. At the top of the column, the mixture of $POMM_1$ and $POMM_2$ is obtained, condensed, and returned to the dissolution autoclave ($POMM_1$ (829 kg) and $POMM_2$ (578 kg)). The mixture of $POMM_{3+}$ is obtained at the bottom of the column. The column bottom fraction is then sent to another distillation column operated under partial vacuum (10 mbar), and at a temperature of 120° C. at the bottom. The mixture of $POMM_3$, $POMM_4$ and $POMM_5$ is distilled and condensed (371 kg of $POMM_3$, 226 kg of $POMM_4$ and 134 kg of $POMM_5$). The mixture of higher POMMs is recovered at the bottom of the column. 77 kg of $POMM_6$, 44 kg of $POMM_7$, 24 kg of $POMM_8$ and 29 kg of POMMs of higher rank are obtained and are returned to the dissolution autoclave.

Example 4: Production of $POMM_{2-4}$ 100 kg of post-industrial polyacetal homopolymer, previously ground into pieces not exceeding 1 cm, are added to 183 kg of fresh dimethoxymethane, at room temperature in an autoclave.

380 kg of $POMM_1$ obtained from a previous operation, and a mixture of 582 kg of sulfolane and 20 kg of a mixture of $POMM_{5+}$ from a previous operation containing 12 kg of $POMM_5$, 5 kg of $POMM_6$, 2 kg of $POMM_7$, 1 kg of $POMM_8$ are also added.

The autoclave is then closed and heated to 80° C. The pressure in the autoclave gradually increases and then stabilizes with the temperature. After about 80 minutes, the dissolved mixture is sent to the reactor, passing over a filter which retains any contaminants and/or undissolved polymer.

In the reactor, a bed of Amberlyst® 15Dry acidic resin was placed on top of a grid. During the first operation, the Amberlyst resin was first washed with methanol and then with dimethoxymethane so as to remove any residual traces of water. In the subsequent operations, this washing is no longer necessary if the resin has not been contaminated with water.

The previously dissolved mixture is sent into the reactor in ascending stream mode, i.e. via the bottom of the reactor. It is dispersed through the catalytic bed via the bottom distribution plate. The acidic resin beads are free to move when the reactor is used in ascending stream mode, but the linear velocity of the liquid is not sufficient to entrain any catalytic particles. The residence time of the liquid mixture in the reactor, i.e. the ratio of the volume of resin (catalytic bed of resin) to the flow rate of polyacetal solution in the $POMM_1$ and the solvent, is 30 mins. The temperature of the solution which feeds the reactor is kept below 120° C., and specifically at 80° C. The reactor is operated under a pressure of 5 bar to avoid any boiling of the reaction mixture.

The reaction mixture is then sent to a distillation column. The pressure is returned to atmospheric pressure. Diisopropylethylamine is injected into the solution to neutralize the acidity caused by the presence of fine catalytic particles (Amberlyst® resin) which are entrained from the reactor.

The temperature at the top of the column is 45° C., and 80° C. at the bottom. At the top of the column, dimethoxymethane is obtained, condensed (380 kg), and returned to the dissolution autoclave. The mixture of $POMM_{2+}$ and sulfolane is obtained at the bottom of the column. The column bottom fraction is then sent to another distillation column operated under partial vacuum (50 mbar). The mixture of $POMM_2$, $POMM_3$ and $POMM_4$ is distilled and condensed (177 kg of $POMM_2$, 76 kg of $POMM_3$ and 31 kg of $POMM_4$). The mixture of higher POMMs is recovered at the bottom of the column. 12 kg of $POMM_5$, 5 kg of $POMM_6$, 2 kg of $POMM_7$, 1 kg of $POMM_8$ and 582 kg of sulfolane are obtained and returned to the dissolution autoclave.

Example 5: Production of $POMM_{3-4}$ 100 kg of post-industrial polyacetal homopolymer, previously ground into pieces not exceeding 0.1 cm, and dried under vacuum at 80° C. for 8 hours, are added to 111 kg of fresh dimethoxymethane, at room temperature in an autoclave. 768 kg of a light mixture of $POMM_1$ (493 kg) and $POMM_2$ (275 kg) obtained from a previous operation, and a mixture of 750 kg of sulfolane and 61 kg of a mixture of $POMM_{5+}$ containing 33 kg of $POMM_5$, 15 kg of $POMM_6$, 7 kg of $POMM_7$, 3 kg of $POMM_8$ and 3 kg of POMMs of higher rank obtained from a previous operation are also added.

The autoclave is then closed and heated to 100° C. The pressure in the autoclave gradually increases and then stabilizes with the temperature. After about 50 minutes, the dissolved mixture is sent to the reactor, passing over a filter which retains any contaminants and/or undissolved polymer.

In the reactor, a bed of Amberlyst® 15Dry acidic resin was placed on top of a grid. During the first operation, the Amberlyst® 15Dry resin was first washed with methanol and then with dimethoxymethane so as to remove any residual traces of water.

The previously dissolved mixture is sent into the reactor in ascending stream mode, i.e. via the bottom of the reactor. It is dispersed through the catalytic bed via the bottom distribution plate. The acidic resin beads are free to move when the reactor is used in ascending stream mode, but the linear velocity of the liquid is not sufficient to entrain any catalytic particles. The residence time of the liquid mixture in the reactor, i.e. the ratio of the volume of resin (catalytic bed of resin) to the flow rate of polyacetal solution in the DMM and the solvent, is 30 mins. The temperature of the solution which feeds the reactor is kept below 120° C., specifically 105° C. here. The reactor is operated under a pressure of 10 bar. The reaction mixture is then sent to a distillation column. The pressure is returned to atmospheric pressure.

The temperature at the top of the column is 105° C., and 120° C. at the bottom. At the top of the column, the mixture of dimethoxymethane ($POMM_1$) and $POMM_2$ is obtained, condensed ($POMM_1$ (493 kg) and $POMM_2$ (275 kg)), and returned to the dissolution autoclave. The mixture of $POMM_{3+}$ and sulfolane is obtained at the bottom of the column. The column bottom fraction is then sent to another distillation column operated under partial vacuum (40 mbar). The mixture of $POMM_3$ and $POMM_4$ is distilled and condensed; 141 kg of $POMM_3$ and 69 kg of $POMM_4$ are recovered as a mixture. The mixture of higher POMMs is recovered at the bottom of the column. 61 kg of a mixture of $POMM_{5+}$ containing 33 kg of $POMM_5$, 15 kg of $POMM_6$, 7 kg of $POMM_7$, 3 kg of $POMM_8$ and 3 kg of POMMs of higher rank and 750 kg of sulfolane are obtained and returned to the dissolution autoclave.

Example 6: Production of $POMM_{3-5}$ 90 g of polyacetal homopolymer, previously finely ground to a particle size not exceeding 0.05 cm, and then dried under a stream of nitrogen at 90° C. overnight, are added to 90 g of fresh dimethoxymethane, at room temperature in an autoclave. 427 g of a light mixture of $POMM_1$ (261 g) and $POMM_2$ (166 g) from a previous operation, and a mixture of 546 g of sulfolane and 31 g of $POMM_{6+}$ containing 15 g of $POMM_6$, 8 g of $POMM_7$, 4 g of $POMM_8$ and 4 g of POMMs of higher rank, obtained from a previous operation, are added.

The autoclave is then closed and heated to 110° C. The pressure in the autoclave gradually increases and then stabilizes with the temperature. After about 30 minutes, the dissolved mixture is sent to the reactor, passing over a filter which retains any contaminants and/or undissolved polymer.

0.25 g of anhydrous methanesulfonic acid is injected into the reactor, which is a pressurized stirred reactor on which is mounted a condenser, operated at 100° C. The reaction is continued for 1 hour, the temperature is then reduced to 15° C., and melamine is injected to neutralize the acid catalyst. The reaction mixture is then filtered to remove the solid particles and is sent to a distillation column. The pressure is returned to atmospheric pressure.

The temperature at the top of the column is 106° C., and 120° C. at the bottom. At the top of the column, 427 g of a light mixture of $POMM_1$ (261 g) and $POMM_2$ (166 g) are condensed and returned to the dissolution autoclave for a subsequent operation. The mixture of $POMM_{3+}$ is obtained at the bottom of the column. The column bottom fraction is then sent to another distillation column operated under partial vacuum (at 8 mbar). The mixture of $POMM_3$, $POMM_4$ and $POMM_5$ is distilled with a high reflux rate and condensed; a mixture of 97 g of $POMM_3$, 54 g of $POMM_4$ and 29 g of $POMM_5$ is recovered. The mixture of higher POMMs is recovered at the bottom of the column. A mixture of 546 g of sulfolane and 31 g of POMMs containing 15 g of $POMM_6$, 8 g of $POMM_7$, 4 g of $POMM_8$ and 4 g of POMMs of higher rank is recovered and returned to the dissolution autoclave.

Example 7: Production of $POMM_{2-8}$ 150 kg of post-production polyacetal homopolymer, previously ground into pieces not exceeding 1 cm and dried under vacuum at 80° C. to remove any residual traces of water, are added to 475 kg of fresh dimethoxymethane ($POMM_1$) sold by the company Lambiotte (Belgium), at room temperature in an autoclave. 832 kg of $POMM_1$ and 101 kg of $POMM_2$ obtained from the distillation of a previous recycling step are also added cold (20° C.) to the autoclave. The autoclave is then closed and heated to 100° C. The pressure in the autoclave gradually increases and then stabilizes at less than 6 bar with the temperature. After about 60 minutes, the dissolved mixture is sent to the reactor, passing over a filter which retains any contaminants and/or undissolved polymer.

In the reactor, a bed of Amberlyst® 15Dry acidic resin (DuPont) was placed on top of a grid. The Amberlyst® 15Dry resin (1325 kg) was first washed with methanol and then dimethoxymethane so as to remove any residual traces of water. Washing is not necessary if the resin has already been washed in a previous step, and if it has not been contaminated with water. The previously dissolved mixture is sent to the reactor in ascending stream mode. It is dispersed through the catalytic bed via the bottom distribution plate. The acidic resin beads are free to move when the reactor is used in ascending stream mode, but the linear velocity of the liquid is not sufficient to entrain any catalytic particles. The residence time of the liquid mixture in the reactor, i.e. the ratio of the volume of resin (catalytic bed of resin) to the flow rate of polyacetal solution in the reactive POMM mixture, is 1 hour. The temperature of the solution which feeds the reactor is kept below 120° C. and notably at 100° C. The reactor is operated under a pressure of 8 bar to prevent any boiling of the reaction solution.

The reaction mixture is then sent to a distillation column. The pressure is reduced to atmospheric pressure and the temperature is lowered to 25° C. A concentrated sodium hydroxide solution is added to neutralize the traces of acidic resin that have been entrained with the reaction mixture. The mixture is then conveyed into the distillation step.

The temperature at the top of the column is 42° C., and 80° C. at the bottom, and the pressure is then gradually reduced to continue the distillation. At the top of the column, dimethoxymethane and part of the $POMM_2$ is obtained, condensed, and returned to the dissolution autoclave (832 kg of $POMM_1$ and 101 kg of $POMM_2$) for the next operation. The mixture of $POMM_{2-8+}$ is obtained at the bottom of the column. A mixture containing 179 kg of $POMM_2$, 120 kg of $POMM_3$, 49 kg of $POMM_4$, 19 kg of $POMM_5$, 7 kg of $POMM_6$, 3 kg of $POMM_7$, 1 kg of $POMM_8$ and less than 1 kg of POMMs of higher rank is obtained. The mass composition is thus 47% by weight of $POMM_2$, 32% by weight of $POMM_3$, 13% by weight of $POMM_4$, 5% by weight of $POMM_5$, 2% by weight of $POMM_6$, 1% by weight of $POMM_7$, 0.3% by weight of $POMM_8$ and less than 1% by weight of POMMs of higher rank.

The invention claimed is:

1. A process of recycling polyacetal containing from 8 to 100,000 carbon atoms for the production of a produced polyoxymethylene dialkyl ether of formula $R—(OCH_2)_n—OR'$, in which R and R' independently represent a methyl group or an ethyl group and n is an integer greater than or equal to 1, the process comprising reacting an acid catalyst with a mixture comprising a polyacetal containing from 8 to 100,000 carbon atoms, a reactive polyoxymethylene dialkyl ether of formula $R—(OCH_2)_k—OR'$ in which R and R' are as defined above and k is an integer greater than or equal to 1, and a solvent and removing by distillation some or all light compounds of formula $R—(OCH_2)_n—OR'$ with n=1 and optionally n=2.

2. The process as claimed in claim 1, further comprising filtering the polyacetal and/or the mixture.

3. The process as claimed in claim 1, further comprising recovering or purifying the produced polyoxymethylene dialkyl ether.

4. The process as claimed in claim 3, in which recovering allows for-separation of the produced polyoxymethylene dialkyl ether from heavy compounds of formula $R—(OCH_2)_n—OR'$ with n greater than a maximum n value of the produced polyoxymethylene dialkyl ether.

5. The process as claimed in claim 3, in which recovering is performed by distillation.

6. The process as claimed in claim 1, further comprising recycling to reintroduce a portion of compounds of formula $R—(OCH_2)_n—OR'$ with n greater than or equal to 1 as reactive polyoxymethylene dialkyl ether.

7. The process as claimed in claim 6, in which recycling reintroduces all or some light compounds removed in distilling and/or all or some heavy compounds removed in recovering as reactive polyoxymethylene dialkyl ether.

8. The process as in claim 1, further comprising synthesizing (meth)acrylic acid or ester or (meth)acrolein or neopentyl glycol from the produced produced polyoxymethylene dialkyl ether.

9. The process as claimed in claim 1, in which the reactive polyoxymethylene dialkyl ether comprises methylal and/or ethylal.

10. The process as claimed in claim 1, in which the reactive polyoxymethylene dialkyl ether comprises methylal and/or ethylal and one or more compounds of formula $R—(OCH_2)_k—OR'$ with k greater than or equal to 2.

11. The process as claimed in claim 1, in which the produced polyoxymethylene dialkyl ether is selected from the group consisting of $CH_3—(OCH_2)—OCH_3$, $CH_3—(OCH_2)_2—OCH_3$, $CH_3—(OCH_2)_3—(OCH)_3$, $CH_3—(OCH_2)_4—OCH_3$, $CH_3—(OCH_2)_5—OCH3$, $CH_3—(OCH_2)_6—OCH_3$, $CH_3—(OCH_2)_7—OCH_3$, $CH_3—(OCH_2)_8—OCH_3$, $C_2H_5—(OCH_2)—OC_2H_5$, $C_2H_5—(OCH_2)_2—OC_2H_5$, $C_2H_5—(OCH_2)_3—OC_2H_5$, $C_2H_5—(OCH_2)_4—OC_2H_5$, $C_2H_5—(OCH_2)_5—OC_2H_5$, $C_2H_5—(OCH_2)_6—OC_2H_5$, $C_2H_5—(OCH_2)_7—OC_2H_5$, $C_2H_5—(OCH_2)_8—OC_2H_5$ and mixtures thereof.

12. The process as claimed in claim 1, in which the produced polyoxymethylene dialkyl ether is:

a mixture of compounds of formula $CH_3—(OCH_2)_n—OCH_3$ with n=2 to 8, a mixture of compounds of formula $CH_3—(OCH_2)_n—OCH_3$ with n=2 to 4, a mixture of compounds of formula $CH_3—(OCH_2)_n—OCH_3$ with n=3 to 5, or a mixture of compounds of formula $CH_3—(OCH_2)_n—OCH_3$ with n=3 to 8, a mixture of compounds of formula $C_2H_5—(OCH_2)_n—OC_2H_5$ with n=2 to 4.

13. The process as claimed in claim 1, in which the polyacetal is a homopolymer.

14. The process as claimed in claim 1, in which a ratio of mass of reactive polyoxymethylene dialkyl ether to mass of polyacetal is at least 2:1.

15. The process as claimed in claim 1, in which the acid catalyst is selected from the group consisting of acidic resins, organic or mineral acids, trifluoromethanesulfonic acid, perchloric acid, methanesulfonic acid, para-toluenesulfonic acid, and sulfuric acid, Lewis acids, $BF_3$, $AsF_5$, acidic mixed oxides, $WO_3/TiO_2$, phosphate alumina, tungsten alumina, zeolites and mixtures thereof.

16. The process as claimed in claim 1, in which the solvent is selected from the group consisting of sulfolane, methylsulfolane, ethylsulfolane, diethysulfolane, propylsulfolane, dipropylsulfolane, butylsulfolane, dibutylsulfolane, pentylsulfolane, dipentylsulfolane, hexylsulfolane, octylsulfolane, DMSO and mixtures thereof.

17. A process for synthesizing (meth)acrylic acid or ester or (meth)acrolein or neopentyl glycol, comprising reacting a produced polyoxymethylene dialkyl ether obtained by the process as claimed in claim 1.

* * * * *